US011167992B2

(12) United States Patent
Yang et al.

(10) Patent No.: US 11,167,992 B2
(45) Date of Patent: Nov. 9, 2021

(54) METHOD FOR PREPARING GRAPHENE BY LIQUID-PHASE BALL MILLING EXFOLIATION

(71) Applicant: GUANGZHOU SPECIAL PRESSURE EQUIPMENT INSPECTION AND RESEARCH INSTITUTE, Guangzhou (CN)

(72) Inventors: Bo Yang, Guangzhou (CN); Shuanghong Zhang, Guangzhou (CN); Maodong Li, Guangzhou (CN); Wei Zhai, Guangzhou (CN); Fang Wen, Guangzhou (CN); Yue Li, Guangzhou (CN); Huachao Guo, Guangzhou (CN); Zhigang Wang, Guangzhou (CN); Guojia Huang, Guangzhou (CN); Shiping Li, Guangzhou (CN); Zhenling Wu, Guangzhou (CN); Yingyi He, Guangzhou (CN)

(73) Assignee: GUANGZHOU SPECIAL PRESSURE EQUIPMENT INSPECTION AND RESEARCH INSTITUTE, Guangzhou (CN)

( * ) Notice: Subject to any disclaimer, the term of this patent is extended or adjusted under 35 U.S.C. 154(b) by 324 days.

(21) Appl. No.: 16/458,588

(22) Filed: Jul. 1, 2019

(65) Prior Publication Data
US 2020/0010325 A1  Jan. 9, 2020

(30) Foreign Application Priority Data
Jul. 6, 2018  (CN) .......................... 201810738621.8

(51) Int. Cl.
*C01B 32/19* (2017.01)
*C01B 32/192* (2017.01)
(Continued)

(52) U.S. Cl.
CPC ............ *C01B 32/19* (2017.08); *C01B 32/192* (2017.08); *C01G 49/10* (2013.01); *C01P 2004/03* (2013.01); *C07C 275/02* (2013.01)

(58) Field of Classification Search
None
See application file for complete search history.

(56) References Cited

U.S. PATENT DOCUMENTS

| 2,928,856 | A | * | 3/1960 | Harwood | ............... | A01N 33/04 |
| | | | | | | 514/499 |
| 3,716,591 | A | * | 2/1973 | Brady | ..................... | C07C 17/02 |
| | | | | | | 570/247 |

(Continued)

FOREIGN PATENT DOCUMENTS

| CN | 105060283 A | 11/2015 |
| CN | 105800603 A | 7/2016 |

(Continued)

*Primary Examiner* — Joseph D Anthony
(74) *Attorney, Agent, or Firm* — Schmeiser, Olsen & Watts, LLP

(57) ABSTRACT

Provided is a method for preparing graphene by liquid-phase ball milling exfoliation, including following steps: mixing a transition metal halide salt, a nitrogen source substance and an organic solvent to prepare an intercalation agent; mixing the intercalation agent with graphite, carrying out ball milling, and then performing centrifugation to obtain a graphite intercalation compound; washing and filtering the graphite intercalation compound obtained, adding an expansion agent, and carrying out ultrasonic agitation to obtain a graphene dispersion; and washing, filtering and drying the graphene dispersion to obtain graphene powder.

13 Claims, 2 Drawing Sheets

(51) Int. Cl.
  *C01G 49/10* (2006.01)
  *C07C 275/02* (2006.01)

(56) References Cited

U.S. PATENT DOCUMENTS

| | | | | |
|---|---|---|---|---|
| 4,593,116 | A * | 6/1986 | Stammann | C07C 269/00 544/37 |
| 6,008,309 | A * | 12/1999 | Baumann | C07C 5/03 528/9 |
| 10,279,393 | B2 * | 5/2019 | Reed | B01J 13/0026 |
| 2009/0022649 | A1 * | 1/2009 | Zhamu | C01B 32/22 423/415.1 |
| 2009/0211914 | A1 * | 8/2009 | Huang | C25D 3/56 205/289 |
| 2013/0101497 | A1 * | 4/2013 | Makhmutov | C01B 32/225 423/448 |
| 2016/0103126 | A1 * | 4/2016 | Muir | G01N 33/54353 530/391.1 |
| 2018/0171161 | A1 * | 6/2018 | Tadamasa | C09D 163/00 |
| 2020/0010325 | A1 * | 1/2020 | Yang | C01B 32/19 |

FOREIGN PATENT DOCUMENTS

| | | |
|---|---|---|
| CN | 106976870 A | 7/2017 |
| CN | 107973293 A | 5/2018 |

* cited by examiner

METHOD FOR PREPARING GRAPHENE BY LIQUID-PHASE BALL MILLING EXFOLIATION

CROSS-REFERENCE TO RELATED APPLICATIONS

This application claims priority to Chinese Application No. CN 201810738621.8 having a filing date of Jul. 6, 2018, the entire contents of which are hereby incorporated by reference.

FIELD OF TECHNOLOGY

The following relates to the field of graphene preparing technology, and in particular relates to a method for preparing graphene by liquid-phase ball milling exfoliation.

BACKGROUND

Graphene has excellent properties such as high electron mobility, ultrahigh thermal conductivity, good mechanical properties, and remarkable room-temperature Hall effect, which enables graphite and graphene related materials to be widely used in battery electrode materials, semiconductor devices, transparent displays, sea-water desalination, hydrogen storage materials, aerospace, composite materials, etc. In view of the excellent properties of graphene materials and their potential application value, the research and application development of graphene continues to heat up at home and abroad. Researchers focus on trying different methods in different fields to prepare high-quality graphene materials on a large scale, and reducing graphene preparation costs by continuously optimizing and improving the graphene preparation process, so that their excellent properties can be applied more widely.

Recently, some progress has been made on how to prepare high-quality graphene materials, but how to achieve mass production of high-yield and high-quality graphene is still a difficulty in research. Ball milling is a mechanical exfoliation method. The preparation of graphene by ball milling has attracted widespread attention from researchers due to its simple production process, low production cost, high yield and good quality.

The known art discloses a graphene preparation method, in which intercalation is carried out by using a composite intercalation agent first, and then exfoliation is achieved by ball milling shear to prepare graphene. In the preparation technology, a surfactant with a high boiling point is used in the preparation process of the composite intercalation agent, which is unfavorable for the subsequent drying treatment and thus affects the graphene quality; moreover, as the ultrasonic intercalation is carried out before ball milling, the preparation process is complicated, and the long-time ultrasonication not only affects the intercalation, but also causes the intercalation agent to fall off from the space between the layers, which is not conducive to the exfoliation of graphene, resulting in a low yield and low quality of the prepared graphene.

The known art also discloses a method for preparing graphene, in which intercalation is also carried out before ball milling, and an acid having strong oxidizing property and another oxidizing agent are used as an intercalation agent, and an expansion agent used therein is also an oxidizing substance. This method is essentially no different from the preparation of graphene by redox, does not reduce the defect degree of graphene, but also is more complicated than the redox preparation method.

According to the above description, the preparation of graphene by ball milling at present mainly adopts a preparation scheme of pre-intercalation and then ball milling, and generally uses a surfactant and enhancer and other experimental conditions that affect or destroy the graphene quality, in the preparation process, resulting in a low yield and low quality of the prepared graphene.

SUMMARY

An aspect relates to a method for preparing graphene by liquid-phase ball milling exfoliation, by means of which high-quality and high-yield graphene can be obtained, and the method is energy-saving and environmentally friendly.

The aspect is achieved by the technical solution: a method for preparing graphene by liquid-phase ball milling exfoliation in embodiments of the present invention, including the following steps:

S1: mixing a transition metal halide salt, a nitrogen source substance and an organic solvent to prepare an intercalation agent;

S2: mixing the intercalation agent obtained in the step S1 with graphite, carrying out ball milling, and then performing centrifugation to obtain a graphite intercalation compound;

S3: washing and filtering the graphite intercalation compound obtained in the step S2, adding an expansion agent, and carrying out ultrasonic agitation to obtain a graphene dispersion; and S4: washing, filtering and drying the graphene dispersion obtained in the step S3 to obtain graphene powder.

Compared with the known art, embodiments of the present invention have the following beneficial effects:

(1) The intercalation agent is prepared by using the synergistic effect among the transition metal halide salt, the nitrogen source substance and the organic solvent, wherein the transition metal halide salt can form a eutectic with the nitrogen source substance or the organic solvent, and the melting point thereof is lower than that of each component, and the mixed intercalation agent is even liquid at room temperature, and is inserted into graphite to form the graphite intercalation compound, thereby lowering the reaction temperature, and the preparation cost and difficulty; and a hydrogen bond can also be formed between the nitrogen source substance and the organic solvent, so that the bonding structure of the nitrogen source substance and the organic solvent is present stably between the graphene layers, thereby avoiding interlayer stacking of the prepared graphene, thus improving the exfoliation efficiency and the product quality.

(2) In the subsequent expansion treatment, under the ultrasonic effect, the expansion agent moves to the space between the graphite layers and decomposes to generate a gas, so that the interlayer spacing of graphite is further increased, which is beneficial to further exfoliation of graphite, thereby greatly improving the yield of graphene.

(3) The intercalation agent does not undergo a chemical reaction during the ball milling process, and the intercalation agent and the graphite intercalation compound can be separated by centrifugation, and the separated intercalation agent can be recycled, which is energy-saving and environmentally friendly.

Further, in the step S1, the mass ratio of the transition metal halide salt, the nitrogen source substance and the organic solvent is (1-10):1:(2-10).

Further, the transition metal halide salt is any one or more of manganese chloride, chromium chloride, copper chloride, nickel chloride, ferrous bromide, ferric bromide, ferric chloride, and ferric chloride hexahydrate. As an electron-accepting intercalator, the transition metal halide salt accepts π electrons between the graphite layers during the intercalation process, and becomes negative ions and enters the space between the graphite layers.

Further, the nitrogen source substance is any one or more of urea, dicyandiamide and melamine. Under the action of nitrogen source such as urea, the edges of graphite can be doped with nitrogen to form functional groups such as pyrrole and pyridine, so that the edges of the graphite layers turn up, thereby facilitating inserting the intercalation agent and the expansion agent between the layers to achieve interlayer exfoliation of graphite.

Further, the organic solvent is any one or more of ethanol, ethylene glycol, isopropanol, 1,2-propanediol, glycerol, formic acid, acetic acid, methyl acetate, ethyl acetate and ethyl formate. The organic solvent is added to achieve a buffering effect in the ball milling process, thereby avoiding damage to the graphene structure by the solid-phase ball milling; moreover, it can disperse and stabilize the graphene obtained by exfoliation to prevent re-stacking of the graphene.

Further, in the step S2, the mass ratio of the intercalation agent to the graphite is (40-200):1.

Further, in the step S2, zirconia balls are used in the ball milling process, and the volume ratio of the intercalation agent to the zirconia balls is (1-3): 1, and the total volume of the intercalation agent and the zirconia balls accounts for 25-60% of the volume of the jar mill. The ball milling speed is 200-700 rpm, and the ball milling time is 2-48 hours. By setting the conditions, it is ensured that the intercalation agent can completely submerge the zirconia balls, so that the zirconia balls can fully exert the shearing action between the balls; while fully shearing, the liquid-phase ball milling can increase the buffering effect of the balls and graphite flakes, and reduce the defects of the produced graphene layers, thereby obtaining a high-yield, large-flake graphene material.

Further, in the step S2, the graphite is any one or more of expanded graphite, expandable graphite, natural flake graphite and graphite powder.

Further, in the step S3, the expansion agent is any one or more of hydrogen peroxide, sodium borohydride and ammonium bicarbonate. The expansion agent decomposes between the layers to generate a gas, which destroys the van der Waals force between the graphite layers, so that the interlayer spacing of graphite is further increased, thereby exfoliating graphene.

Further, in the step S4, the drying is carried out at a temperature of 60-80° C. for 12-24 hours.

For the sake of better understanding and implementation, embodiments of the present invention are described in detail below in conjunction with the accompanying drawings.

BRIEF DESCRIPTION

Some of the embodiments will be described in detail, with reference to the following figures, wherein like designations denote like members, wherein.

DETAILED DESCRIPTION

Figure 1:
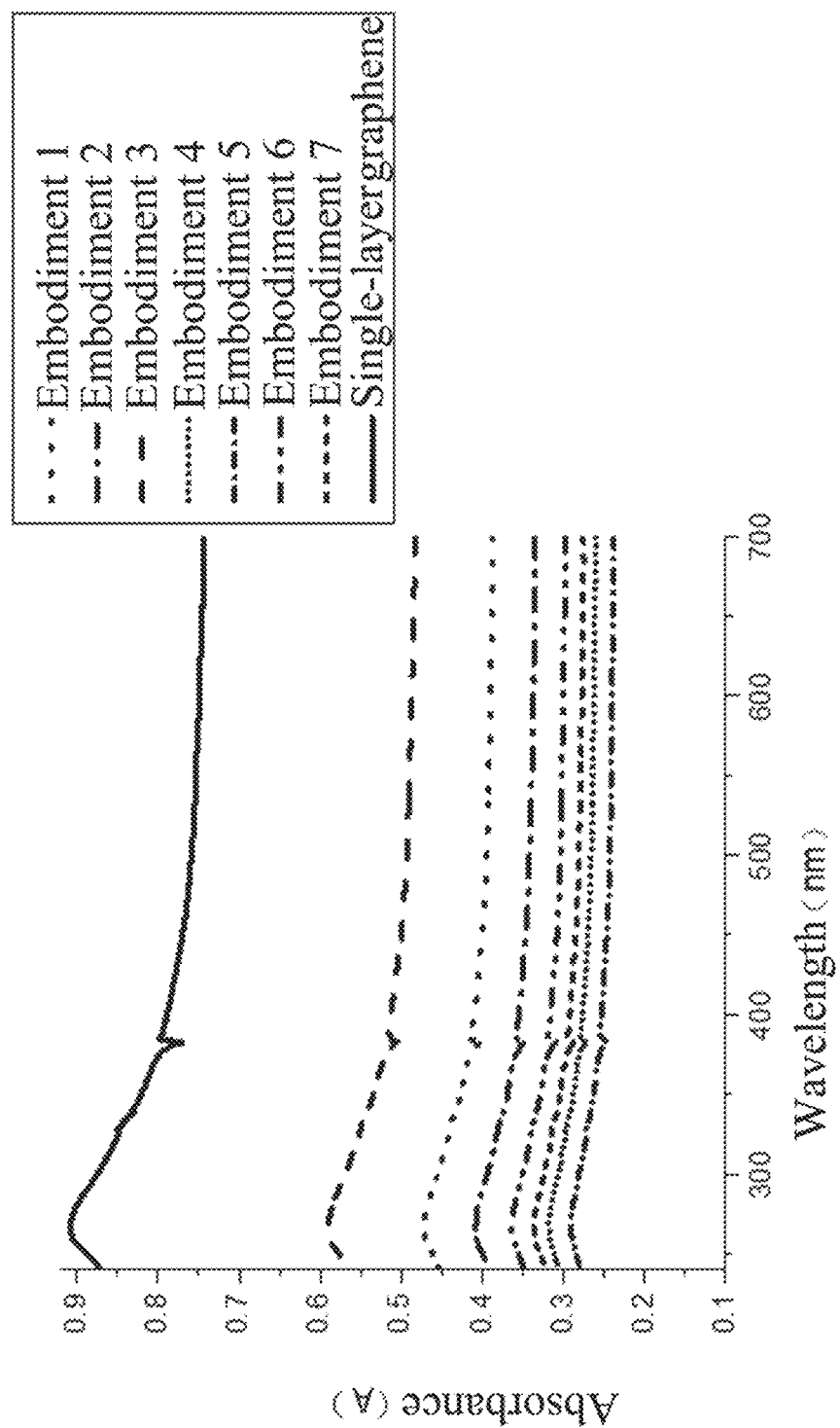
FIG. 1 illustrates ultraviolet absorbances of graphene dispersions of Embodiments 1 to 7 and a comparative single-layer graphene dispersion.

In view of the problems in the preparation of graphene by the ball milling method at present that defects are serious and an organic solvent with a high boiling point is difficult to remove, in embodiments of the present invention, the intercalation agent is changed to a transition metal halide salt and a nitrogen source substance without strong oxidizing property and an organic solvent that is easy to remove, which are used in combination as an environmentally friendly intercalation agent, which has an intercalating effect during ball milling and achieves partial exfoliation, so that the complicated process of ball milling after intercalation can be avoided; then simple cleaning is carried out to remove the intercalation agent on the surface of the intercalation compound; after filtering, the intercalation compound is further subjected to expansion treatment to obtain high-quality and high-yield graphene. The operation is simple and the production cost is low, which are favorable for promoting the mass production of graphene. Moreover, the corrosion effect of a strong oxidant on ajar mill is avoided, thereby achieving the combination of the intercalation and the ball-milling exfoliation process, which not only improves the exfoliation efficiency, but also can maintain the integrity of the graphene crystal structure, thus expanding the applications of graphene in the fields of energy storage materials, biomaterials and the like.

The method for preparing graphene by liquid-phase ball milling exfoliation in embodiments of the present invention includes the following the steps:

S1: mixing a transition metal halide salt, a nitrogen source substance and an organic solvent to prepare an intercalation agent;

S2: mixing the intercalation agent obtained in the step S1 with graphite, carrying out ball milling, and then performing centrifugation to obtain a graphite intercalation compound;

S3: washing and filtering the graphite intercalation compound obtained in the step S2, adding an expansion agent, and carrying out ultrasonic agitation to obtain a graphene dispersion; and S4: washing, filtering and drying the graphene dispersion obtained in the step S3 to obtain graphene powder.

Specifically, in the step S1, the mass ratio of the transition metal halide salt, the nitrogen source substance and the organic solvent is (1-10):1:(2-10). The transition metal halide salt is any one or more of manganese chloride, chromium chloride, copper chloride, nickel chloride, ferrous bromide, ferric bromide, ferric chloride, and ferric chloride hexahydrate. The nitrogen source substance is any one or more of urea, dicyandiamide and melamine. The organic solvent is any one or more of ethanol, ethylene glycol, isopropanol, 1,2-propanediol, glycerol, formic acid, acetic acid, methyl acetate, ethyl acetate and ethyl formate.

In the step S2, the mass ratio of the intercalation agent to the graphite is (40-200):1. Zirconia balls are used in the ball milling process, and the volume ratio of the intercalation agent to the zirconia balls is (1-3): 1, and the total volume of the intercalation agent and the zirconia balls accounts for 25-60% of the volume of ajar mill. The ball milling speed is 200-700 rpm, and the ball milling time is 2-48 hours. The speed during centrifugation is 8000-10000 rpm. The graphite is any one or more of expanded graphite, expandable graphite, natural flake graphite and graphite powder.

In the step S3, the expansion agent is any one or more of hydrogen peroxide, sodium borohydride and ammonium bicarbonate. The agitating speed is 200-600 r/min.

In the step S4, the drying process is carried out by using a vacuum oven for drying at a temperature of 60-80° C. for 12-24 hours.

Further description is provided below in conjunction with specific embodiments.

Embodiment 1

1 g of expanded graphite was poured into a dry jar mill, then 10 g of ferric chloride, 10 g of urea, 20 g of isopropanol were mixed uniformly and poured into the jar mill so that zirconia beads were submerged therein; the jar mill was fixed symmetrically to a planetary ball mill, the rotating speed was adjusted to 700 rpm, and ball milling was carried out continuously for 48 hours; after the ball milling, the graphite intercalation compound was separated from the intercalation agent by high-speed centrifugation at 10,000 rpm, and then the intercalation compound was simply washed with water to remove the intercalation agent on the surface of the graphite intercalation compound; after filtration, a filter cake was placed into a flask, 50 ml of 5% hydrogen peroxide was added therein, water-bath sonication was carried out for 20 min, and the solution was stirred for 2 h to decompose hydrogen peroxide; then the mixture was filtered, washed 3 times, and dried at 80° C. for 12 h to obtain graphene powder.

0.06 g of the obtained graphene powder was dispersed in a 50 mg/ml aqueous urea solution to prepare a graphene dispersion with a concentration of 0.024 mg/ml. Then, moderate sonication was carried out for 15 min, and the absorbance of the graphene dispersion at 270 nm was measured by ultraviolet-visible spectroscopy and compared with the absorbance of a prepared single-layer graphene dispersion with the same concentration at 270 nm to measure the concentration of graphene and calculate the yield of graphene.

The single-layer graphene for comparison was purchased from Nanjing XFNANO Materials Tech Co., Ltd, and the model of the graphene was XF001W.

Embodiment 2

1 g of 300-mesh flake graphite was poured into a dry jar mill, then 5 g of copper chloride, 5 g of urea, 50 g of absolute ethanol were mixed uniformly and poured into the jar mill so that zirconia beads were submerged therein. The jar mill was fixed symmetrically to a planetary ball mill, the rotating speed was adjusted to 500 rpm, and ball milling was carried out continuously for 48 hours; after the ball milling, the graphite intercalation compound was separated from the intercalation agent by high-speed centrifugation at 10,000 rpm, and then the intercalation compound was simply washed with water to remove the intercalation agent on the surface of the graphite intercalation compound; after filtration, a filter cake was placed into a flask, 50 ml of 5% sodium borohydride solution was added therein, water bath sonication was carried out for 20 min, then the pH of the solution was adjusted to make the solution acidic, and stirring was carried out for 2 h to decompose sodium borohydride; then the mixture was filtered, washed 3 times, and dried at 60° C. for 24 h to obtain graphene powder.

0.06 g of the obtained graphene powder was dispersed in a 50 mg/ml aqueous urea solution to prepare a graphene dispersion with a concentration of 0.024 mg/ml. Then, moderate sonication was carried out for 15 min, and the absorbance of the graphene dispersion at 270 nm was measured by ultraviolet-visible spectroscopy and compared with the absorbance of a prepared single-layer graphene dispersion with the same concentration at 270 nm to measure the concentration of graphene and calculate the yield of graphene.

The single-layer graphene for comparison was purchased from Nanjing XFNANO Materials Tech Co., Ltd, and the model of the graphene was XF001W.

Embodiment 3

1 g of graphite powder was poured into a dry jar mill, then 50 g of ferric chloride hexahydrate, 5 g of urea, 10 g of ethylene glycol were mixed uniformly and poured into the jar mill so that zirconia beads were submerged therein; the jar mill was fixed symmetrically to a planetary ball mill, the rotating speed was adjusted to 400 rpm, and ball milling was carried out continuously for 48 hours; after the ball milling, the graphite intercalation compound was separated from the intercalation agent by high-speed centrifugation at 10,000 rpm, and then the intercalation compound was simply washed with water to remove the intercalation agent on the surface of the graphite intercalation compound; after filtration, a filter cake was placed into a flask, 50 ml of 5% hydrogen peroxide was added therein, water-bath sonication was carried out for 20 min, and the solution was stirred for 2 h to decompose hydrogen peroxide; then the mixture was filtered, washed 3 times, and dried at 80° C. for 12 h to obtain graphene powder.

0.06 g of the obtained graphene powder was dispersed in a 50 mg/ml aqueous urea solution to prepare a graphene dispersion with a concentration of 0.024 mg/ml. Then, moderate sonication was carried out for 15 min, and the absorbance of the graphene dispersion at 270 nm was measured by ultraviolet-visible spectroscopy and compared with the absorbance of a prepared single-layer graphene dispersion with the same concentration at 270 nm to measure the concentration of graphene and calculate the yield of graphene.

The single-layer graphene for comparison was purchased from Nanjing XFNANO Materials Tech Co., Ltd, and the model of the graphene was XF001W.

Embodiment 4

1 g of graphite powder was poured into a dry jar mill, then 20 g of chromium chloride, 5 g of melamine, 20 g of ethylene glycol, and 10 g of glycerin were mixed uniformly and poured into the jar mill so that zirconia beads were submerged therein; the jar mill was fixed symmetrically to a planetary ball mill, the rotating speed was adjusted to 600 rpm, and ball milling was carried out continuously for 48 hours; after the ball milling, the graphite intercalation compound was separated from the intercalation agent by high-speed centrifugation at 10,000 rpm, and then the intercalation compound was simply washed with hot water to remove the intercalation agent on the surface of the graphite intercalation compound; after filtration, a filter cake was placed into a flask, 50 ml of 5% ammonium bicarbonate was added therein, water-bath sonication was carried out at 75° C. for 20 min, and the solution was stirred for 2 h; then the mixture was filtered, washed 3 times, and dried at 80° C. for 12 h to obtain graphene powder.

0.06 g of the obtained graphene powder was dispersed in a 50 mg/ml aqueous urea solution to prepare a graphene dispersion with a concentration of 0.024 mg/ml. Then, moderate sonication was carried out for 15 min, and the absorbance of the graphene dispersion at 270 nm was measured by ultraviolet-visible spectroscopy and compared with the absorbance of a prepared single-layer graphene dispersion with the same concentration at 270 nm to measure the concentration of graphene and calculate the yield of graphene.

The single-layer graphene for comparison was purchased from Nanjing XFNANO Materials Tech Co., Ltd, and the model of the graphene was XF001W.

Embodiment 5

1 g of expandable graphite was poured into a dry jar mill, then 25 g of nickel chloride, 5 g of dicyandiamide, 50 g of methyl acetate were mixed uniformly and poured into the jar mill so that zirconia beads were submerged therein; the jar mill was fixed symmetrically to a planetary ball mill, the rotating speed was adjusted to 400 rpm, and ball milling was carried out continuously for 48 hours; after the ball milling, the graphite intercalation compound was separated from the intercalation agent by high-speed centrifugation at 10,000 rpm, and then the intercalation compound was simply washed with hot water to remove the intercalation agent on the surface of the graphite intercalation compound; 50 ml of 5% sodium borohydride solution was added therein, water bath sonication was carried out for 20 min, then the pH of the solution was adjusted to make the solution acidic, and stirring was carried out for 2 h to decompose sodium borohydride; then the mixture was filtered, washed 3 times, and dried at 80° C. for 12 h to obtain graphene powder.

0.06 g of the obtained graphene powder was dispersed in a 50 mg/ml aqueous urea solution to prepare a graphene dispersion with a concentration of 0.024 mg/ml. Then, moderate sonication was carried out for 15 min, and the absorbance of the graphene dispersion at 270 nm was measured by ultraviolet-visible spectroscopy and compared with the absorbance of a prepared single-layer graphene dispersion with the same concentration at 270 nm to measure the concentration of graphene and calculate the yield of graphene.

The single-layer graphene for comparison was purchased from Nanjing XFNANO Materials Tech Co., Ltd, and the model of the graphene was XF001W.

Embodiment 6

1 g of expanded graphite was poured into a dry jar mill, then 10 g of ferrous bromide, 10 g of urea, and 50 g of ethyl acetate were mixed uniformly and poured into the jar mill so that zirconia beads were submerged therein; the jar mill was fixed symmetrically to a planetary ball mill, the rotating speed was adjusted to 500 rpm, and ball milling was carried out continuously for 48 hours; after the ball milling, the graphite intercalation compound was separated from the intercalation agent by high-speed centrifugation at 10,000 rpm, and then the intercalation compound was simply washed with ethanol to remove the intercalation compound on the surface of the graphite intercalation compound; after filtration, a filter cake was placed into a flask, 50 ml of 5% ammonium bicarbonate was added therein, water-bath sonication was carried out at 75° C. for 20 min, and the solution was stirred for 2 h; then the mixture was filtered, washed 3 times, and dried at 60° C. for 24 h to obtain graphene powder.

0.06 g of the obtained graphene powder was dispersed in a 50 mg/ml aqueous urea solution to prepare a graphene dispersion with a concentration of 0.024 mg/ml. Then, moderate sonication was carried out for 15 min, and the absorbance of the graphene dispersion at 270 nm was measured by ultraviolet-visible spectroscopy and compared with the absorbance of a prepared single-layer graphene dispersion with the same concentration at 270 nm to measure the concentration of graphene and calculate the yield of graphene.

The single-layer graphene for comparison was purchased from Nanjing XFNANO Materials Tech Co., Ltd, and the model of the graphene was XF001W.

Embodiment 7

1 g of 300-mesh flake graphite was poured into a dry jar mill, then 25 g of ferric chloride, 25 g of nickel chloride, 5 g of urea, 50 g of ethanol were mixed uniformly and poured into the jar mill so that zirconia beads were submerged therein; the jar mill was fixed symmetrically to a planetary ball mill, the rotating speed was adjusted to 600 rpm, and ball milling was carried out continuously for 48 hours; after the ball milling, the graphite intercalation compound was separated from the intercalation agent by high-speed centrifugation at 10,000 rpm, and then the intercalation compound was simply washed with water to remove the intercalation agent on the surface of the graphite intercalation compound; after filtration, a filter cake was placed into a flask, 50 ml of 5% hydrogen peroxide was added therein, water-bath sonication was carried out for 20 min, and the solution was stirred for 2 h to decompose hydrogen peroxide; then the mixture was filtered, washed 3 times, and dried at 80° C. for 12 h to obtain graphene powder.

0.06 g of the obtained graphene powder was dispersed in a 50 mg/ml aqueous urea solution to prepare a graphene dispersion with a concentration of 0.024 mg/ml. Then, moderate sonication was carried out for 15 min, and the absorbance of the graphene dispersion at 270 nm was measured by ultraviolet-visible spectroscopy and compared with the absorbance of a prepared single-layer graphene dispersion with the same concentration at 270 nm to measure the concentration of graphene and calculate the yield of graphene.

The single-layer graphene for comparison was purchased from Nanjing XFNANO Materials Tech Co., Ltd, and the model of the graphene was XF001W.

The absorbance of the graphene dispersions of Embodiments 1 to 7 and the absorbance of the single-layer graphene dispersion for comparison were detected, and the results are shown in FIG. 1. The graphene yields of Embodiments 1 to 7 were calculated, and the results are shown in Table 1 below.

TABLE 1

Summary of reagent types and graphene yields of Embodiments 1-7

| Embodiment | intercalation agent | Graphite | Expansion agent | Graphene yield |
|---|---|---|---|---|
| 1 | Ferric chloride, urea, isopropanol | Expanded graphite | Hydrogen peroxide | 52% |
| 2 | Copper Chloride, urea, absolute ethanol | 300-mesh flake graphite | Sodium borohydride solution | 45% |
| 3 | Ferric chloride hexahydrate, urea, ethylene glycol | Graphite powder | Hydrogen peroxide | 65% |
| 4 | Chromium chloride, melamine, ethylene glycol, glycerin | Grapliite powder | Ammonium bicarbonate solution | 35% |
| 5 | Nickel chloride, dicyandiamide, methyl acetate | Expandable graphite | Sodium borohydride solution | 32% |
| 6 | Ferrous bromide, urea, ethyl acetate | Expanded graphite | Ammonium bicarbonate solution | 40% |
| 7 | Ferric chloride, nickel chloride, urea, ethanol | 300-mesh flake graphite | Hydrogen peroxide | 37% |

It can be seen from FIG. 1 that the final ball-milled graphene yields in the different embodiments are different, wherein the yield in Embodiment 3 is the highest, which is attributed to the good synergistic effect of ferric chloride hexahydrate, urea and ethylene glycol.

Figure 2:
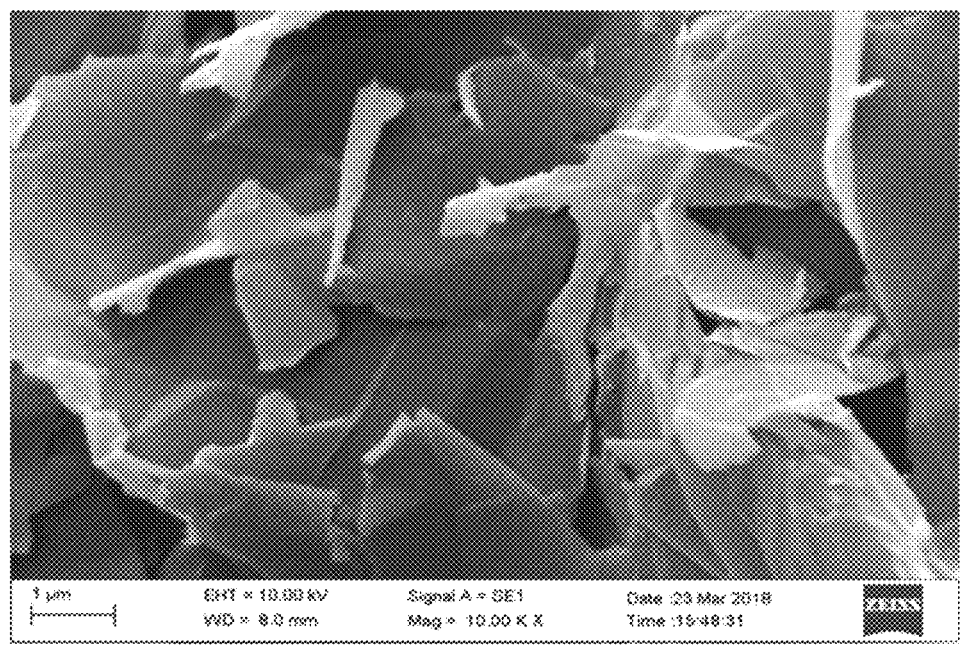
FIG. 2 shows a scanning electron microscope image of expanded graphite in Embodiment 1.
Figure 3:
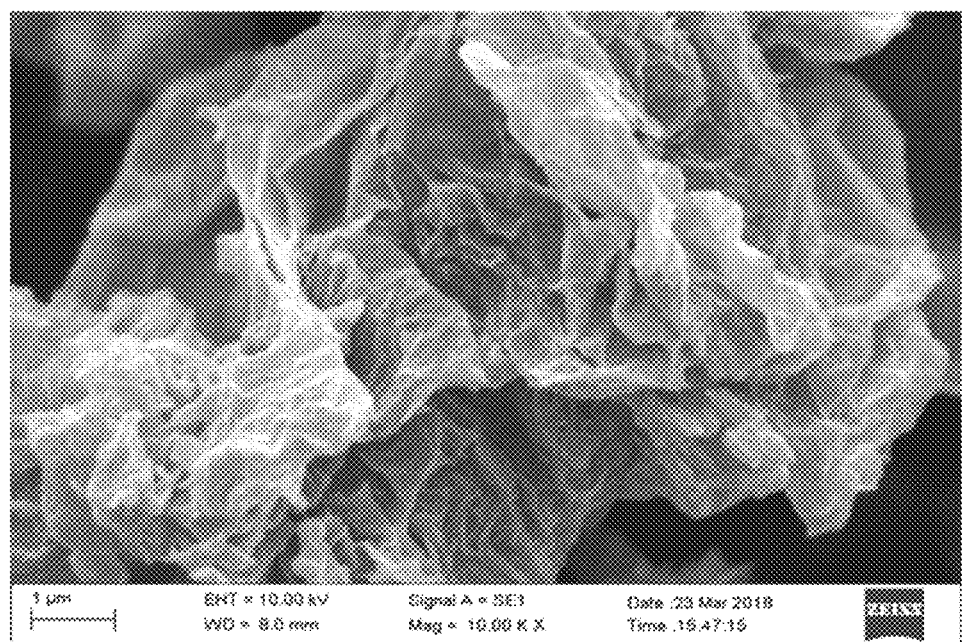
FIG. 3 shows a scanning electron microscope image of a graphene product in Embodiment 1.

In addition, the morphology of the expanded graphite and the graphene product in Embodiment 1 was tested to obtain a scanning electron microscope (SEM) image, as shown in FIGS. 2 and 3, wherein at the same magnification (10 K times), the surface of expanded graphite (as shown in FIG. 2) is smooth and exhibits irregular-size flake structures, while the ball-milled graphene (shown in FIG. 3) has flexibility and obvious pleats, with some graphene layers folded and stacked on each other.

Compared with the known art, embodiments of the present invention have the following beneficial effects:

(1) The intercalation agent is prepared by using the synergistic effect among the transition metal halide salt, the nitrogen source substance and the organic solvent, wherein the transition metal halide salt can form a eutectic with the nitrogen source substance or the organic solvent, and the melting point thereof is lower than that of each component, and the mixed intercalation agent is even liquid at room temperature, and is inserted into graphite to form the graphite intercalation compound, thereby lowering the reaction temperature, and the preparation cost and difficulty; and a hydrogen bond can also be formed between the nitrogen source substance and the organic solvent, so that the bonding structure of the nitrogen source substance and the organic solvent is present stably between the graphene layers, thereby avoiding interlayer stacking of the prepared graphene, thus improving the exfoliation efficiency and the product quality.

(2) In the subsequent expansion treatment, under the ultrasonic effect, the expansion agent moves to the space between the graphite layers and decomposes to generate a gas, so that the interlayer spacing of graphite is further increased, which is beneficial to further exfoliation of graphite, thereby greatly improving the yield of graphene.

(3) The intercalation agent does not undergo a chemical reaction during the ball milling process, and the intercalation agent and the graphite intercalation compound can be separated by centrifugation, and the separated intercalation agent can be recycled, which is energy-saving and environmentally friendly.

Although the present invention has been disclosed in the form of preferred embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

What is claimed:

1. A method for preparing graphene by liquid-phase ball milling exfoliation, comprising following steps:
    mixing a transition metal halide salt, a nitrogen source substance and an organic solvent to prepare an intercalation agent;
    mixing the intercalation agent obtained with graphite, carrying out ball milling, and then performing centrifugation to obtain a graphite intercalation compound;
    washing and filtering the graphite intercalation compound, adding an expansion agent, and carrying out ultrasonic agitation to obtain a graphene dispersion; and
    washing, filtering and drying the graphene dispersion to obtain graphene powder.

2. The method of claim 1, wherein the mass ratio of the transition metal halide salt, the nitrogen source substance and the organic solvent is (1-10):1:(2-10).

3. The method of claim 1, wherein the transition metal halide salt is any one or more of manganese chloride, chromium chloride, copper chloride, nickel chloride, ferrous bromide, ferric bromide, ferric chloride, and ferric chloride hexahydrate.

4. The method of claim 2, wherein the transition metal halide salt is any one or more of manganese chloride, chromium chloride, copper chloride, nickel chloride, ferrous bromide, ferric bromide, ferric chloride, and ferric chloride hexahydrate.

5. The method of claim 3, wherein the nitrogen source substance is any one or more of urea, dicyandiamide and melamine.

6. The method of claim 4, wherein the nitrogen source substance is any one or more of urea, dicyandiamide and melamine.

7. The method of claim 3, wherein the organic solvent is any one or more of ethanol, ethylene glycol, isopropanol, 1,2-propanediol, glycerol, formic acid, acetic acid, methyl acetate, ethyl acetate and ethyl formate.

8. The method of claim 4, wherein the organic solvent is any one or more of ethanol, ethylene glycol, isopropanol, 1,2-propanediol, glycerol, formic acid, acetic acid, methyl acetate, ethyl acetate and ethyl formate.

9. The method of claim 1, wherein the mass ratio of the intercalation agent to the graphite is (40-200):1.

10. The method of claim 9, wherein zirconia balls are used in the ball milling process, and the volume ratio of the intercalation agent to the zirconia balls is (1-3):1, and the total volume of the intercalation agent and the zirconia balls accounts for 25-60% of the volume of the jar mill, and wherein the ball milling speed is 200-700 rpm, and the ball milling time is 2-48 hours.

11. The method of claim 1, wherein the graphite is any one or more of expanded graphite, expandable graphite, natural flake graphite and graphite powder.

12. The method of claim 1, wherein the expansion agent is any one or more of hydrogen peroxide, sodium borohydride and ammonium bicarbonate.

13. The method of claim 1, wherein in the drying is carried out at a temperature of 60-80° C. for 12-24 hours.

* * * * *